United States Patent [19]

Haas et al.

[11] Patent Number: 4,617,387
[45] Date of Patent: Oct. 14, 1986

[54] BISMORPHOLINES AND A PROCESS FOR THEIR PREPARATION

[75] Inventors: Peter Haas, Haan; James M. Barnes, Wermelskirchen; Wilhelm Goyert, Leverkusen, all of Fed. Rep. of Germany

[73] Assignee: Bayer Aktiengesellschaft, Bayerwerk, Fed. Rep. of Germany

[21] Appl. No.: 640,907

[22] Filed: Aug. 15, 1984

[30] Foreign Application Priority Data

Aug. 31, 1983 [DE] Fed. Rep. of Germany ....... 3331436

[51] Int. Cl.⁴ ............................................ C07D 265/28
[52] U.S. Cl. ........................................ 544/74; 524/198
[58] Field of Search .......................................... 544/74

[56] References Cited

U.S. PATENT DOCUMENTS

| | | | |
|---|---|---|---|
| 3,193,523 | 7/1965 | Neumann et al. | 260/45.9 |
| 3,193,524 | 7/1965 | Holtschmidt et al. | 260/45.9 |
| 3,594,387 | 7/1971 | Metzger | 260/307 |
| 3,689,499 | 9/1972 | Metzger | 260/307 F |
| 3,770,693 | 11/1973 | Metzger | 260/45.8 |
| 3,795,638 | 3/1974 | Grogler | 260/45.9 |

FOREIGN PATENT DOCUMENTS

| | | |
|---|---|---|
| 610969 | 3/1962 | Belgium . |
| 1231975 | 5/1971 | United Kingdom . |

OTHER PUBLICATIONS

Rakhmankulov et al, Chemical Abstracts, vol. 87 (1977), 201553c.

Dieck et al, Chem. Ber., vol. 117, No. 2 (Feb. 1984), pp. 694–701.

*Primary Examiner*—Richard L. Raymond
*Attorney, Agent, or Firm*—Gene Harsh; Joseph C. Gil; Thomas W. Roy

[57] ABSTRACT

The present invention relates to 2,3,2',3'-bis-morpholine derivatives corresponding to the formula

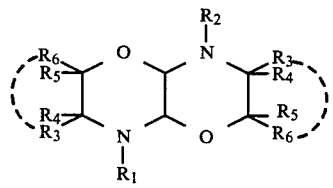

The present invention also relates to a process for the preparation of these derivatives and to their use as hydrolysis protective agents for synthetic polymers containing ester groups and/or carbonate groups. Preferred synthetic polymers are polyurethanes.

7 Claims, No Drawings

BISMORPHOLINES AND A PROCESS FOR THEIR PREPARATION

BACKGROUND OF THE INVENTION

1. Field of the Invention

The present invention is directed to novel bismorpholine derivatives, a process for their production and their use as hydrolysis inhibitors in polymers containing ester and/or carbonate groups.

2. Description of the Prior Art

It is well known that ester groups (including carbonate groups) may undergo hydrolytic decomposition to revert to the starting components. In the case of relatively high molecular weight substances prepared from components containing ester groups, such reaction causes degradation of the polymer chain which generally results in a loss of mechanical properties. A further disadvantage is the autocatalytic destruction by the continuous formation of new carboxylic acid groups which becomes progressively more drastic.

The reaction of polyesters with isocyanates which are at least bifunctional results in polyurethanes which are widely used industrially as high quality elastomers. In order to protect the superior quality of these polymers against degradation by moist heat, water or steam, it has long been customary to use hydrolysis protective agents such as the group of substances known as carbodiimides which are described in DE-PS 1,005,726 and in BE-PS 610,969, 612,040 and 733,573. FR-PS 1,450,919 discloses iminooxazolidines corresponding to the formula

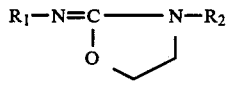

wherein
$R_1$ = aryl,
$R_2$ = aryl, alkyl
as age protective agents for compounds containing ester groups. In both cases, however, the tendency to migration, the deleterious effects on the compression set and the catalytic effects (change in the casting and pot life of polyurethanes) are found to be disadvantageous.

Although the hydroxyalkylurea derivatives described in DE-PS 2,106,726 are found to be quite effective, the high melting points and low solubilities of compounds of this type in polyesters or short chain chain lengthening agents are found to be disadvantageous.

It is an object of the present invention to provide hydrolysis protective agents which do not suffer from the previously discussed disadvantages.

A group of hydrolysis protective agents which have no connection with previously known classes of compounds as regards the course of the reactions and the structure and material properties of the reaction products has now been found completely unexpectedly and must be given a decidedly positive assessment as regards their processing characteristics. These compounds, which have not hitherto been described and which act as hydrolysis protective agents (HSM), are reaction products of glyoxal and aminoethanols substituted with organic groups. The products are cycloacetals as hereinafter described.

SUMMARY OF THE INVENTION

The present invention relates to 2,3,2',3'-bis-morpholine derivatives corresponding to the formula

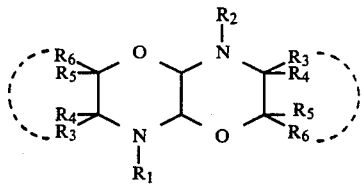

wherein
$R_1$ and $R_2$ may be identical or different and represent alkyl, alkenyl, cycloalkyl or aryl substituents, preferably $C_1$ to $C_7$-alkyl or $C_5$ or $C_6$-cycloalkyl, most preferably methyl or cyclohexyl, and $R_3$, $R_4$, $R_5$ and $R_6$ represent hydrogen, alkyl, alkenyl, cycloalkyl and/or aryl substituents, preferably $C_1$-$C_7$-alkyl substituents, or a cycloalkylene or arylene substituent formed by linkage of $R_3$ and $R_6$ with aminoethanol, $R_4$ and $R_5$ being omitted in the case of arylene substituents.

The cycloalkyl or aryl groups (preferably benzene groups) may also carry inert substituents such as $C_1$-$C_7$-alkyl, chlorine or bromine.

The present invention also relates to a process for the preparation of 2,3,2',3'-bismorpholine derivatives from
(a) glyoxal and
(b) N-monosubstituted aminoethanols of the type

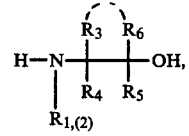

wherein $R_1$, $R_2$, $R_3$, $R_4$, $R_5$ and $R_6$ have the meaning described above, $R_4$ and $R_5$ being omitted in the case of arylene groups, by reaction of the components (reaction ratio preferably about 1:2) in aqueous solution or in solvents containing water, at temperatures preferably up to the boiling point of water at the prevailing pressure, preferably at about 40° C. to 100° C.

The present invention also relates to the use of 2,3,2',3'-bismorpholines as hydrolysis protective agents for synthetic polymers containing ester groups and/or carbonate groups, in particular polyurethanes containing ester groups and/or carbonate groups and obtained from polyisocyanates, polyols containing ester groups and/or carbonate groups, preferably relatively high molecular weight polyols of this type, and optionally further auxiliary agents and additives, the 2,3,2',3'-bismorpholine derivatives defined by the structure indicated above being used in the polymer in quantities of from about 0.1 to 10 parts, preferably from about 0.3 to 5, most preferably from about 0.5 to 2.5 parts.

DETAILED DESCRIPTION OF THE INVENTION

Since the bismorpholines are readily soluble, they may be added to the starting materials or mixtures thereof. In the case of polyurethanes they may be added either to the relatively high molecular weight polyol and/or to the chain lengthening agents normally used or to mixtures thereof. They may also be incorporated with the finished polymers containing ester and/or carbonate groups, e.g. their melts, solutions or dispersions.
The following are representatives according to the invention of this class of bismorpholine compounds:
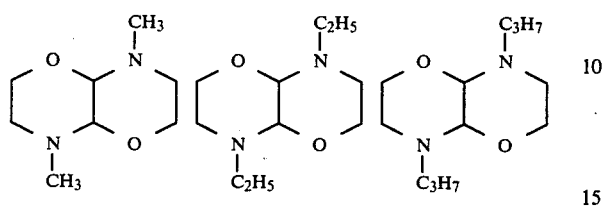
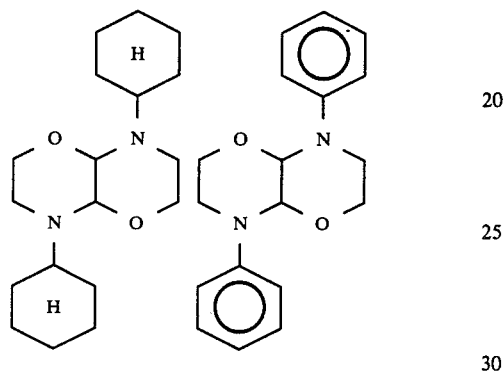
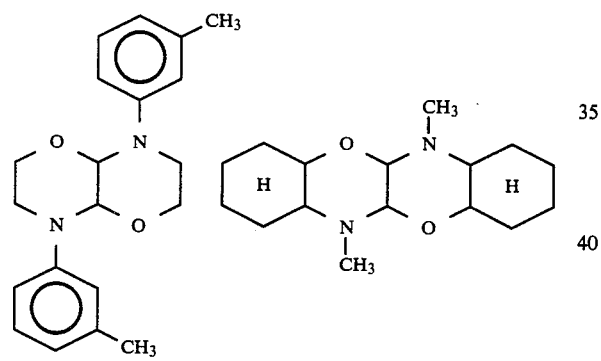
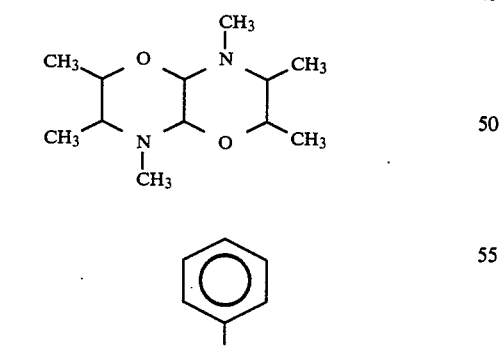
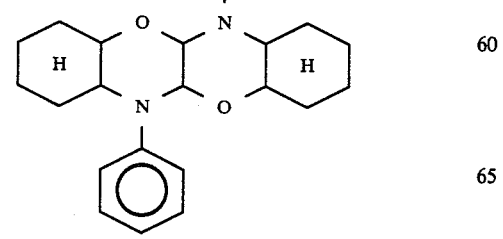
-continued
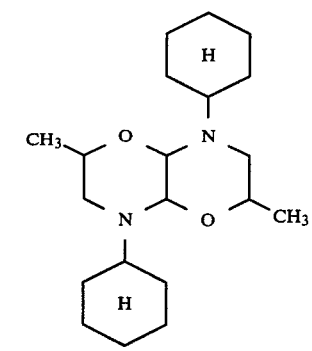
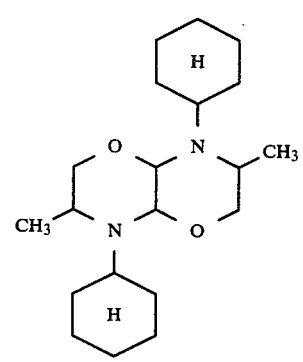
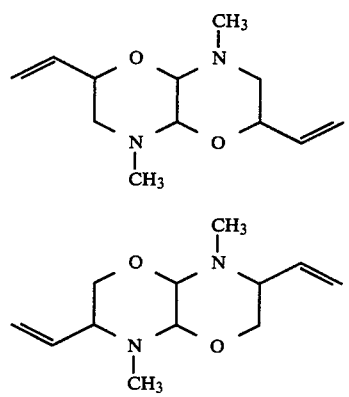
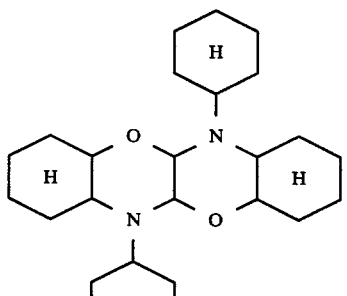
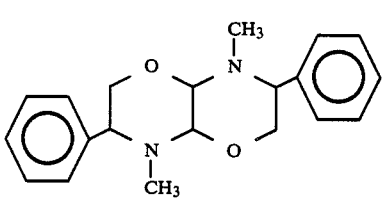

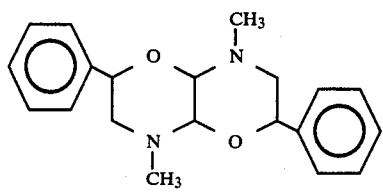

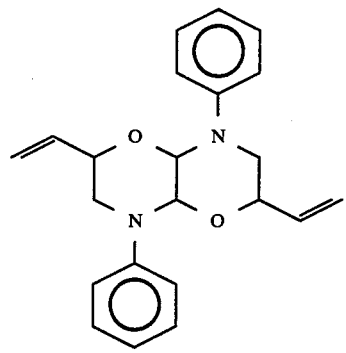

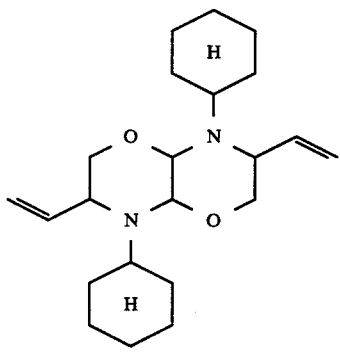

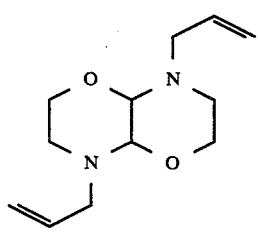

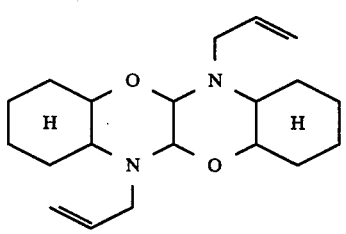

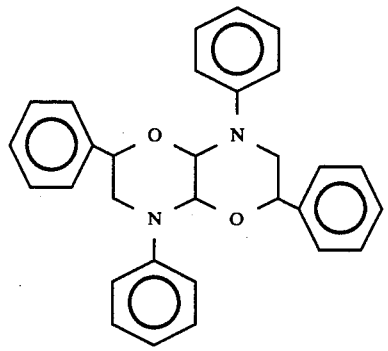

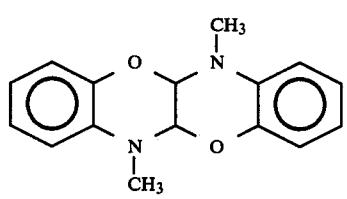

Glyoxal is the preferred bisaldehyde used as a starting compound for the preparation of the bismorpholines and is generally used in the form of its commercially available aqueous solution.

The following are examples of suitable N-mono-substituted β-aminoalcohols: N-methyl-ethanolamine, N-ethyl-ethanolamine, N-propyl-ethanolamine, N-cyclohexyl-ethanolamine, 2-hydroxyethyl-aniline, 3-methylhydroxyethyl-aniline, 2-(N-methylamino)-buten-(3)-ol-(1), N-methylamino-2-hydroxy-butene-(3), 2-(N-phenylamino)-buten-(3-ol-(1), N-phenylamino-2-hydroxybutene-(3), 2-(N-methylamino)-2-phenyl-ethanol, 2-(N-methylamino)-1-phenyl-ethanol, 2-(N-phenylamino)-2-phenyl-ethanol, 2-(N-phenylamino)-1-phenyl-ethanol, 2-(N-phenylamino)-cyclohexanol-(1), 2-(N-cyclohexylamino)-cyclohexanol-(1), 1-(N-phenyl)-2-hydroxy-propylamine, 1-(N-cyclohexyl)-2-hydroxypropylamine, 2-methylamino-cyclohexanol, N-hydroxyethyl-cyclohexylamine and 1-(N-methyl)-2-hydroxypropylamine, or mixtures thereof.

The glyoxal and β-aminoalcohols are preferably reacted together in stoichiometric quantities (1:2) since if one of the components is used in excess, the compounds according to the invention are still formed in the quantity corresponding to that of the other component. The reaction is preferably carried out in aqueous solution, and the reaction products, especially those of the more highly substituted representatives, precipitate after brief heating, e.g. at about 40°–100° C., whereas the methyl or ethyl derivatives may be obtained virtually quantitatively with the high degree of purity by concentration of their solution by partial evaporation. The reaction may also be carried out in aqueous-organic solvents, e.g. aqueous alcohols, ethers, ketones or similar compounds.

According to the invention, the products may be used in particular for stabilizing polyurethanes containing ester groups and/or carbonate groups. These polyurethanes containing ester and/or carbonate groups include any polyurethanes prepared from polyols containing ester groups and/or carbonate groups, i.e. polyurethane foams, polyurethane elastomers, coating compounds based on polyurethanes, adhesives, grouting compounds, etc. Such polyurethanes containing ester groups may be synthesized from relatively high molecular weight hydroxypolyesters, hydroxypolylactones, e.g. those based on ε-caprolactones, hydroxypolycarbonates, e.g. hexanediol polycarbonates, and polyethers containing ester or carbonate groups.

Apart from their preferred use of stabilizing polyurethanes containing ester groups and/or polycarbonate groups, the hydrolysis protective agents according to the invention are also suitable for protecting any other synthetic polymers containing ester groups and/or carbonate groups, e.g. polyesters obtained from polycarboxylic acids, preferably dicarboxylic acids such as phthalic acid, isophthalic acid, terephthalic acid, adipic acid or carbonic acid, and polyhydric alcohols, e.g. ethylene glycol, butanediol, neopentyl glycol, hexanediol, glycerol, 2,2-bis-(4'-hydroxyphenyl)-propane, trimethylolpropane, pentaerythritol, etc. They may also be used for the protection of polymers containing ester groups in side chains or copolymers based on acrylic or methacrylic acid esters or synthetic polymers based on vinyl esters, e.g. polyvinyl acetate, etc. Polycarbonates, e.g. those based on 2,2-bis-(4'-hydroxyphenyl)-propane, may also be stabilized with these substances.

Such polymer products may be, for example, in the form of lacquers, foils, coatings, fibers, foams, elastomers, casting resins or molded products.

The invention is further illustrated, but is not intended to be limited by the following examples in which all parts and percentages are by weight unless otherwise specified.

EXAMPLES (A) Preparation of 2,3,2',3'-bismorpholines (Process and properties)

Example 1

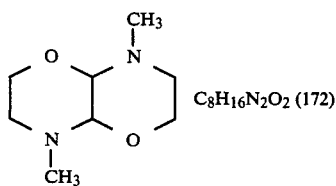

$C_8H_{16}N_2O_2$ (172)

482 g (2.5 mol) of a 30% aqueous glyoxal solution were introduced dropwise into 375 g (5 mol) of methyl ethanolamine, the temperature rising from 75 to 80° C. The reaction mixture was heated to 80° C. for 5 hours and the resulting solution was then concentrated by evaporation so that the bismorpholine slowly crystallized. The residual moisture content was removed by suction filtration and the product was dried. Yield: 735 g, which corresponded to 85% of theoretical yield, melting point 73°–74° C.

The plae yellow product was converted by sublimation into a completely colorless substance melting at 75° C.

Analysis: Calculated: C 55.8, H 9.3, N 16.3; Found: C 55.2, H 9.0, N 16.2.

The molecular ion M+ was observed at 172 in the mass spectrum. The structure was elucidated by high field resonance, the results of which are shown in the Table.

$^1$H data from Example 1 measured at up to 360 MHZ in CDCl$_3$

| Chem. Shift | (ppm) | Coupling constant | J (Hz) |
| --- | --- | --- | --- |
| H$_{2a}$ | 3.673 | 2a, 2e | (−)11.6 |
| H$_{2e}$ | 3.913 | 2e, 3a | 3.6 |
| H$_{3a}$ | 2.893 | 2e, 3e | 1.3 |
| H$_{3e}$ | 2.285 | 2a, 3e | 3.0 |
| H$_5$ | 4.000 | 2a, 3a | 11.5 |
| NCH$_3$ | 2.480 | 3a, 3e | (−)11.5 |

The data obtained corresponded to the morpholine ring[1,2]. This applied particularly to the geminal and vicinal coupling constants.

Example 2

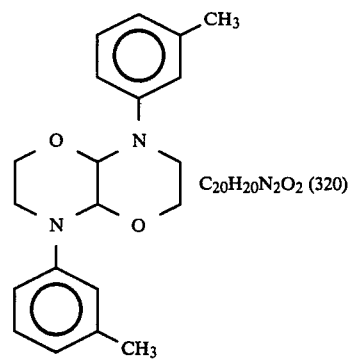

$C_{20}H_{20}N_2O_2$ (320)

75.5 g of 3-methyl-N-hydroxyethyl-aniline were introduced dropwise into 48.5 g of 30% glyoxal solution and the reaction mixture was heated to 80° C. for 2 hours, cooled and suction filtered. The residue was stirred up with 120 ml of methanol at slightly elevated temperature, suction filtered and dried. Yield: 58 g of colorless crystals. Melting point: 151°–152° C.

Analysis: Calculated: C 75.0, H 6.2, N 8.7; Found: C 74.3, H 7.8, N 8.5.

$^1$H data in CDCl$_3$ at 360 MHz for the morpholine portion

| Chem. Shift | (ppm) | Coupling Constant | J (Hz) |
| --- | --- | --- | --- |
| H$_{2a}$ | 3.857 | 2a, 2e | −11.6 |
| H$_{2e}$ | 4.073 | 2e, 3a | 3.6 |
| H$_{3a}$ | 3.500 | 2e, 3e | 1.4 |
| H$_{3e}$ | 3.077 | 2a, 3e | 2.9 |
| H$_5$ | 5.062 | 2a, 3a | 11.5 |
|  |  | 3a, 3e | −11.9 |

(1) W. B. Smith and B. A. Shoulders, J. Phys. Chem. 69, 579 (1965)

(2) J. Devilliers, H. D. Giao and J. Novech, Compt. Rend. 277C, 1067 (1973).

The structure of the morpholine derivative was thus confirmed as in Example 1.

Example 3

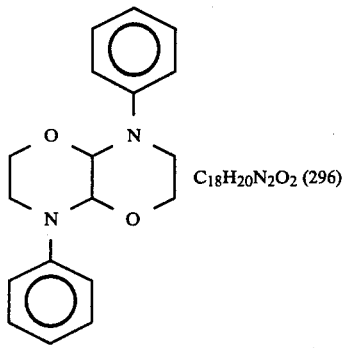

C₁₈H₂₀N₂O₂ (296)

137 g of 2-hydroxyethyl-aniline were introduced dropwise into 96.8 g of a 30% glyoxal solution and the reaction mixture heated to 80° C. for 2 hours, cooled, suction filtered, heated in 250 ml of methanol, suction filtered and dried. Yield: 89 g of colorless crystals, m.p. 163° C.

Analysis: Calculated: C 73.0, H 6.7, N 9.45; Found: C 71.4, H 6.5, N 8.9.

Example 4

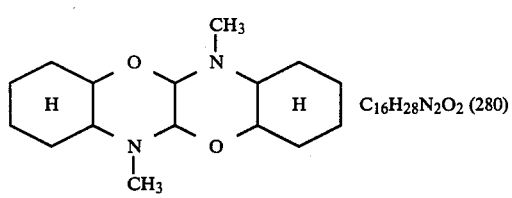

C₁₆H₂₈N₂O₂ (280)

65 g of 2-methylamino-cyclohexanol were introduced dropwise into 48.5 g of a 30% aqueous glyoxal solution and the reaction mixture was heated to 80° C. for 3 hours and then concentrated by evaporation, dried on clay and recrystallized from 70 ml of methanol. Yield: 24 g of colorless crystals, m.p. 111°–113° C.

Analysis: Calculated: C 68.5, H 10.0, N 10.0; Found: C 68.8, H 9.0, N 9.9.

Example 5

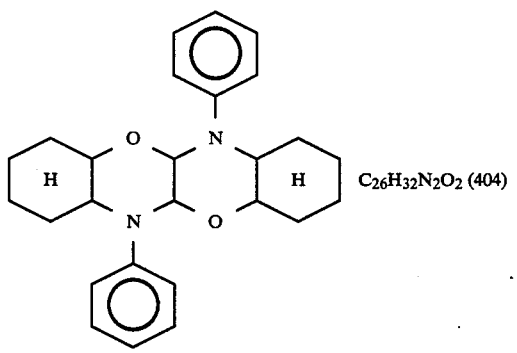

C₂₆H₃₂N₂O₂ (404)

19.4 g of a 30% glyoxal solution and 38.2 g of 2-phenylamino-cyclohexanol were heated to 100° C. for 2.5 hours, decanted from the water, stirred up with a small quantity of methanol, suction filtered and dried. Yield: 15 g of colorless crystals, m.p. 198°–199° C.

Analysis: Calculated: C 77.2, H 7.9, N 6.95; Found: C 76.0, H 7.5, N 6.5.

Example 6

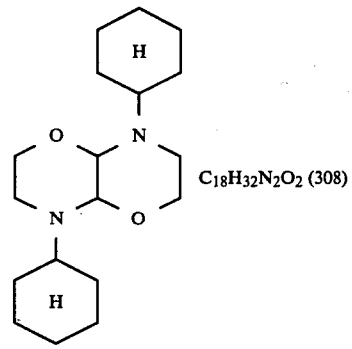

C₁₈H₃₂N₂O₂ (308)

57.2 g of N-hydroxyethyl-cyclohexylamine were introduced dropwise into 38.8 g of a 30% glyoxal solution at 25° C. and the reaction mixture was heated to 70° C. for 4 hours. The product was recrystallized from methanol after suction filtration. Yield: 44 g (72% of theoretical) of colorless needles, m.p. 95°–97° C.

Analysis: Calculated: C 70.0, H 10.4, N 9.1; Found: C 69.9, H 10.0, N 9.1.

(B) Use as hydrolysis protective agent

Example 7

7.1 Standard polyurethane without hydrolysis protective agent (Comparison)

100 parts by weight of a polyester of adipic acid and ethylene glycol having an average molecular weight of 2000 and an OH number of 56 were dehydrated under a vacuum of about 40 mm at 130° C. and then maintained at about 130° C.

25 parts by weight of 1,5-diisocyanatonaphthalene were then added. After about 2 minutes, a vacuum of about 40 mm is applied. After termination of the exothermic reaction, 5 parts by weight of butane-1,4-diol were added to the prepolymer with vigorous stirring. The prepolymer was stirred for about 30 seconds and poured into a mold which had been preheated to 110° C. The mixture remained pourable for about 60 seconds and solidified after about 9 minutes.

The elastomer was then tempered for 24 hours at 110° C. At the end of this time it has the properties indicated in Table 1.

After storage in water at 80° C. (Standard test rod S1 according to DIN 53504 used as sample), the tensile strength, tension at 100% and elongation at break after 0, 7, 9 and 11 days were again measured (see Table 2).

Example 8

Use as hydrolysis protective agent in polyurethane elastomers.

An isocyanate prepolymer was prepared as described in Example 7. After termination of the exothermic reaction, a mixture of 0.6 parts by weight of 4,4'-dimethyl-2,3,2',3'-bismorpholine according to Example 1 in 5 parts by weight of butane-1,4-diol was added to the isocyanate prepolymer with vigorous stirring and the mixture was worked up as in Example 7.

The tensile strength, tension at 100% and elongation at break were again measured after storage in water at 80°

C. (Standard rod S1 according to DIN 53 504 used as test sample) (see Table 2).

The stabilizing effect of 2,3,2',3'-bismorpholine was particularly pronounced in the strength and elongation values obtained after 11 days' storage in water at 80° C.

EXAMPLE 9

(Comparison with a known hydrolysis protective agent)

When 0.85 parts of 2,2',6,6'-tetraisopropyldiphenyl carbodiimide were used instead of the compound according to the invention described in Example 8, the values shown below (see Table 2) were obtained in the hydrolysis test.

The comparison values show that the class of compounds according to the invention were superior in their effect to a conventional, widely industrially used stabilizer.

Example 10

The isocyanate prepolymer was prepared as in Example 7. After termination of the exothermic reaction, a mixture of 0.8 parts by weight of the product obtained according to Example 6 and 5.0 parts by weight of butane-1,4-diol were added to the prepolymer with vigorous stirring. The mixture was stirred for about 30 seconds and poured into a mold which had been preheated to 110° C. The mixture was pourable for about 50 seconds and solidified after about 9 minutes.

The elastomer was then tempered for 24 hours at 110° C. At the end of this time, it had the properties shown in Table 1.

After storage in water at 80° C. (Standard rod S1 according to DIN 53 504 used as test sample), the tensile strength, tension at 100% and elongation at break were again measured (see Table 2).

TABLE 1

| | | | Properties of polyester polyurethanes (before hydrolysis) | | | | | |
|---|---|---|---|---|---|---|---|---|
| | | Test | Example No. | | | | | |
| | Unit of measurement | standard according to DIN | 7 (Comparison) | 8 | 9 (Comparison) | 10 | 11 | 12 | 13 |
| Shore hardness A/D | — | 53505 | 91/37 | 90/35 | 90/36 | — | 85 | 90 | 85 |
| Tension at 100% | MPa | 53504 | 8.65 | 8.26 | 8.44 | — | — | — | — |
| Tensile strength | MPa | 53504 | 47.0 | 44.5 | 46.7 | — | 39 | 49.6 | 38 |
| Elongation at break | % | 53504 | 719 | 700 | 716 | — | 570 | 550 | 580 |
| Tear propagation strength | kN/m | 53513 | 73 | 78 | 77 | — | — | — | — |
| Impact elasticity | % | 53512 | 54 | 53 | 54 | — | 46 | 49 | 47 |
| Tear propagation resistance | kN/m | 53515 | — | — | — | — | 78 | — | 77 |

TABLE 2

| | | | Test standard according to DIN | Properties after hydrolysis in water | | | |
|---|---|---|---|---|---|---|---|
| | | Unit of Measurement | | Storage body, standard rod S1 according to DIN 53504 Storage in water at 80° C. in days (d) after | | | |
| | | | | 0 d | 7 d | 9 d | 11 d |
| Example 7 (Comparison without hydrolysis protective agent) | Tension at 100% | MPa | 53504 | 8.65 | 6.82 | 6.07 | 5.9 |
| | Tensile strength | MPa | 53504 | 47.0 | 27.8 | 11.1 | 8.8 |
| | Elongation at break | % | 53504 | 719 | 690 | 365 | 266 |
| Example 8 (according to the invention) | Tension at 100% | MPa | 53504 | 8.26 | 6.94 | 6.26 | 6.42 |
| | Tensile strength | MPa | 53504 | 44.5 | 34.7 | 25.6 | 22.5 |
| | Elongation at break | % | 53504 | 700 | 778 | 691 | 634 |
| Example 9 Comparison with state of the art | Tension at 100% | MPa | 53504 | 8.44 | 6.78 | 6.44 | 6.40 |
| | Tensile strength | MPa | 53504 | 46.7 | 30.4 | 23.9 | 20.7 |
| | Elongation at break | % | 53504 | 716 | 760 | 701 | 659 |
| Example 10 (according to the invention) | Tension at 100% | MPa | 53504 | good resistance to hydrolysis | | | |
| | Tensile strength | MPa | 53504 | | | | |
| | Elongation at break | % | 53504 | | | | |

TABLE 2a

| | | Unit of measurement | Test standard according to DIN | Hydrolysis test after x days at 100° C. | |
|---|---|---|---|---|---|
| | | | | after 0 d | after 6 d |
| Example 11 (according to the invention) | Tensile strength | MPa | 53504 | 39.0 | 32.0 |
| | Elongation at break | % | 53504 | 570 | 700 |
| Example 12 (according to the invention) | Tensile strength | MPa | 53504 | 49.6 | 20.5 |
| | Elongation at break | % | 53504 | 550 | 688 |
| Example 13 Comparison without additive | Tensile strength | MPa | 53504 | 38.0 | 4.0 |
| | Elongation at break | % | 53504 | 580 | 15 |

Example 11

100 parts by weight of a polyester of butane-1,4-diol and adipic acid (OH number 49.1) were stirred together with 1 part by weight of the hydrolysis protective agent according to Example 1, 0.8 parts by weight of stearylamide and 10 parts by weight of butane-1,4-diol at 120° C. 39.6 parts by weight of 4,4'-diisocyanatodiphenylmethane (ratio of NCO:OH groups=1.03) were heated to 60° C. and added with vigorous stirring to the above solution which had been heated to 120° C. The reactive mixture was then poured onto a metal plate coated with mold release wax. The mixture solidified very rapidly and could be removed from the mold after about 6 minutes. The polymer was then broken down in cutting mills and after 2 to 4 days it was injection molded to produce molded articles which were tempered at 80° C. for 17 hours. These molded products had the physical data shown in Table 1.

The resistance to hydrolysis of this product was particularly marked (Table 2a). After 6 days at 1000° C., this elastomer was technically virtually intact while the Comparison example not containing any 4,4'-dimethyl-2,3,2',3'-bis-morpholine was almost completely destroyed.

Example 12

100 parts by weight of a polyester of butane-1,4-diol and adipic acid (OH number 49.1) were stirred together with 0.5 parts by weight of the hydrolysis protective agent according to Example 6, 0.8 parts by weight of stearylamide and 10 parts by weight of butane-1,4-diol at 120° C. 39.6 parts by weight of 4,4'-diisocyanatodiphenylmethane (ratio of NCO:OH groups=1.03) were heated to 60° C. and added with vigorous stirring to the above solution which had been heated to 120° C. The reactive mixture was then poured on a metal plate covered with mold release wax. The mixture solidified very rapidly and could be removed from the plate after only about 6 minutes. The polymer was broken down in cutting mills and injection molded after 2 to 4 days to form molded products which were then tempered at 80° C. for 17 hours. These molded products have the physical data shown in Table 1.

The good resistance of this product to hydrolysis was particularly noticeable (Table 2a). After 6 days at 100° C., this elastomer was technically still substantially intact while the Comparison example not containing any 4,4'-bis-cyclohexyl-2,3,2',3'-bis-morpholine was almost completely destroyed.

Example 13

The procedure was the same as in Examples 11 and 12 but without the addition of stabilizer according to the invention.

The physical properties tested on this injection molded thermoplast are shown in Tables 1 and 2a.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A 2,3,2',3'-bis-morpholine derivative compound corresponding to the formula:

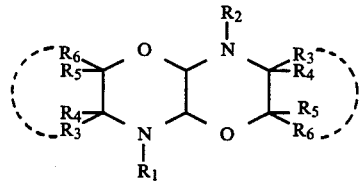

wherein
$R_1$ and $R_2$ may be identical or different and represent methyl or cyclohexyl, the groups
$R_3$ and $R_6$ form a cyclohexane group, while $R_4$ and $R_5$ represent hydrogen and
wherein the cycloalkyl groups may optionally contain inert substituents comprising a member selected from the group consisting of $C_1$-$C_7$-alkyl, chlorine and bromine.

2. A 2,3,2',3'-bis-morpholine derivative compound corresponding to the formula

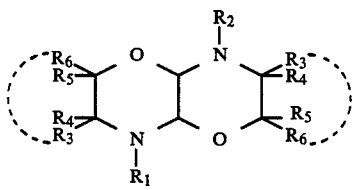

wherein
$R_1$ and $R_2$ represent cyclohexyl and
$R_3$, $R_4$, $R_5$ and $R_6$ represent hydrogen.

3. A process for the preparation of a 2,3,2',3'-bis-morpholine derivative compound according to the formula

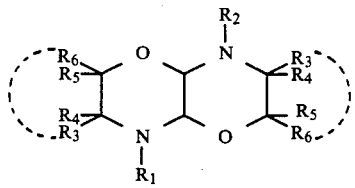

which consists of reacting at a temperature of about 40°–100° C. in aqueous solution or a solvent containing water (a) glyoxal with (b) an N-mono-substituted amino alcohol corresponding to the formula

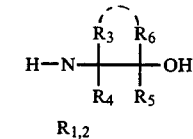

wherein $R_1$ and $R_2$ may be identical or different and represent methyl or cyclohexyl and $R_3$, $R_4$, $R_5$ and $R_6$ represent hydrogen or the groups $R_3$ and $R_6$ form a cyclohexane group while $R_4$ and $R_5$ represent hydrogen and wherein the cycloalkyl groups may optionally contain inert substituents comprising a member selected from the group consisting of $C_1$–$C_7$-alkyl, chlorine and bromine.

4. The process of claim 3 wherein $R_1$ and $R_2$ are identical and represent methyl or cyclohexyl and $R_3$, $R_4$, $R_5$ and $R_6$ represent hydrogen.

5. The process of claim 3 wherein $R_1$ and $R_2$ are identical and represent methyl or cyclohexyl, $R_3$ and $R_6$ form a cyclohexane group and $R_4$ and $R_5$ represent hydrogen.

6. The process of claim 3 wherein $R_1$ and $R_2$ represent methyl and $R_3$, $R_4$, $R_5$ and $R_6$ represent hydrogen.

7. The process of claim 3 wherein the reaction is conducted using a molar ratio of (a):(b) of 1:2.

* * * * *